US007008373B2

(12) United States Patent
Stoianovici et al.

(10) Patent No.: US 7,008,373 B2
(45) Date of Patent: Mar. 7, 2006

(54) SYSTEM AND METHOD FOR ROBOT TARGETING UNDER FLUOROSCOPY BASED ON IMAGE SERVOING

(75) Inventors: Daniel Stoianovici, Baltimore, MD (US); Alexandru Patriciu, Baltimore, MD (US); Louis R. Kavoussi, Lutherville, MD (US)

(73) Assignee: The Johns Hopkins University, Baltimore, MD (US)

( * ) Notice: Subject to any disclaimer, the term of this patent is extended or adjusted under 35 U.S.C. 154(b) by 187 days.

(21) Appl. No.: 10/290,460

(22) Filed: Nov. 8, 2002

(65) Prior Publication Data

US 2003/0120283 A1   Jun. 26, 2003

Related U.S. Application Data

(60) Provisional application No. 60/336,931, filed on Nov. 8, 2001.

(51) Int. Cl.
*A61B 1/00* (2006.01)
(52) U.S. Cl. .......................... 600/101; 600/312; 606/1; 128/899
(58) Field of Classification Search ................ 600/407, 600/312, 101, 427, 160, 113, 181, 478, 1; 128/898, 899; 606/1
See application file for complete search history.

(56) References Cited

U.S. PATENT DOCUMENTS

| 5,078,140 A |   | 1/1992  | Kwoh          |         |
|-------------|---|---------|---------------|---------|
| 5,572,999 A |   | 11/1996 | Funda et al.  |         |
| 5,772,580 A | * | 6/1998  | Utsui et al. ................. | 600/160 |
| 5,806,518 A |   | 9/1998  | Mittelstadt   |         |
| 6,055,449 A |   | 4/2000  | Navab         |         |

OTHER PUBLICATIONS

Loser, M.H. et al., "Visual Servoing for Automatic and Uncalibrated Percutaneous Procedures", Proc. SPIE vol. 3976, pp. 270-281, Medical Imaging 2000: Image Display and Visualization, Seong K. Mun; Ed., published Apr. 2000; 12 pages.

Navab, N. et al., "Visual Servoing for Automatic and Uncalibrated Needle Placement for Percutaneous Procedures", Proc. Of IEEE Conf. On Computer Vision and Pattern Recognition, Jun. 13-15, 2000; Hilton Head Island, South Carolina, USA, 8 pages.

* cited by examiner

*Primary Examiner*—Beverly M. Flanagan
(74) *Attorney, Agent, or Firm*—Arent Fox PLLC

(57) ABSTRACT

A system and method for image guided instrument targeting including a robot unit coupled with an instrument, an imaging unit, and a first control unit, which is coupled with the robot unit and coupled with the imaging unit. The control unit receives the imaging data about a target and about the instrument from the imaging unit and controls the robot unit to properly orienting the instrument for insertion, based upon the imaging data.

10 Claims, 4 Drawing Sheets

FIG. 2: Fluoro-servoing instrument targeting

SYSTEM AND METHOD FOR ROBOT TARGETING UNDER FLUOROSCOPY BASED ON IMAGE SERVOING

CROSS REFERENCE TO RELATED APPLICATION

This application claims priority to provisional patent application No. 60/336,931, entitled A FLUORO-SERVING METHOD FOR ROBOTIC TARGETING OF SURGICAL INSTRUMENTATION, filed on Nov. 8, 2001, the contents of which are incorporated herein by reference.

BACKGROUND OF THE INVENTION

1. Field of the Invention

The present invention relates to robotic devices and methods for instrument targeting. In particular, the invention relates to systems and methods for computer assisted image-based instrument targeting, under portable x-ray fluoroscopy based image servoing.

2. Description of the Related Art

Minimally invasive and noninvasive procedures for surgery are gaining increased popularity mainly due to reduced trauma to patients and improved recovery time. One of the main problems encountered in minimally invasive procedures is, in contrast to open surgical procedures, a dramatic reduction in the surgeon's visual ability. Accordingly, radiological, ultrasonic, and magnetic resonance imaging techniques are employed to map anatomical geometry during intra-operative procedures.

Systems and methods for image guided instrument targeting are known. Manual and computer assisted instrument targeting is known. Some existing methods for computer assisted instrument targeting under fluoroscopy use complex robot-image registration algorithms. However, these same approaches use static images of fiducial markers to estimate robot-image coordinate mapping, which is then used for targeting.

Manual fluoroscopy-guided interventions are normally based on trial and error requiring considerable surgical skill and operative training. Automatic targeting has the potential to reduce the required level of surgical experience and the variability among surgeons in performing this type of procedures.

Portable ultrasonic and fluoroscopy units (commonly termed C-Arms) are ubiquitous in modern operating rooms. Both of these affordable imagers provide real time two-dimensional (2-D) visualization. A common impediment in using these 2-D imagers is the lack of volumetric representation necessitating extensive surgical training for correct 3-D interpretation. The problem of "retrofitting" computer image-based 3-D navigation systems on commonplace C-arms is complicated by the fact that the vast majority of portable fluoroscopy systems do not provide encoding of the C-Arm position or orientation. This creates difficulty in estimating the pose of the imager with respect to the patient, thus complicating computer assisted procedures using this image information. Many solutions have been proposed for helping surgeons in performing fluoroscopy guidance. See Desbat L., Champleboux g., Fleute M., Komarek P., Mennessier C., Monteil B., Rodet T., Bessou P., Coulomb M., Ferretti G., "3D Interventional Imaging with 2D X-Ray Detectors", Medical Image Computing and Computer-Assisted Intervention, September 1999, Cambridge, England: Lecture Notes in Computer Science, Springer-Verlag, Vol. 1679, pp 973–980, 1999; Gueziec A., Kazanzides P., Williams B., Taylor R. H., "Anatomy-Based Registration of CT-Scan and Intraoperative X-Ray Images for Guiding a Surgical Robot", IEEE Transactions on medical Imaging, 17(5):715–728, 1998; the contents of which are incorporated herein by reference.

For example, an efficient algorithm allowing for the complete reconstruction of volumetric anatomy using multiple 2-D images is proposed in Navab, N., Bani-Hashemi, A., Nadar, M. S., Wiesent, K., Durlak, P., Brunner, T., Barth, K., Graumann, R.: "3D Reconstruction from Projection Matrices in a C-Arm Based 3D-Angiography system", 1998 MICCAI, Lecture Notes in Computer Science, Springer-Verlag, Vol. 1679, pp 688–705, 1999; the contents of which are incorporated herein by reference.

Simultaneously, other researchers concentrated on the development of image guidance and registration techniques for various fluoroscopy guided interventions. See Desbat et al., supra; Gueziec et al., supra; Potamiakos, P., Davies, B. L. Hilbert R. D. "Intra-operative imaging guidance for keyhole surgery methodology and calibration", Proc. First Int. Symposium on Medical Robotics and Computer Assisted Surgery, Pittsburgh, Pa. P. 98–104; Stoianovivi, D., Cadedu, J. A., Demaree, R. D., Basile H. A., Taylor, R. Whitcomb, L. L., Sharpe, W. N. Jr., Kavoussi, L. R.: "An efficient Needle Injection Technique and Radiological Guidance Method for Percutaneous Procedures", 1997 CVRMed-MrCas, Lecture Notes in Computer Science, Springer-Verlag, Vol. 1205, pp. 295–298, 1997; the contents of which are incorporated herein by reference.

Most image guided instrument targeting procedures, such as percutaneous needle access, and radio and ultrasonic ablation, require targeting of a specific instrument/probe at an exact organ location. The clinical outcome of these procedures significantly relies on targeting accuracy.

To address this problem, computer-assisted instrument targeting systems have been developed based on specialized image registration algorithms. Such methods commonly use at least two images of a spatial radio-opaque marker of complex geometry or a series of one-dimensional marks distributed on a defined pattern. See Bzostek, A., Schreiner, S., Barnes, A. C., Cadeddu, L. A. Roberts, W., Anderson, J. H., Taylor, R. H., Kavoussi, L. R.: "An automated system for precise percutaneous access of the renal collecting system", Lecture Notes in Computer Science, Springer-Verlag, Vol. 1205, pp. 299–308, 1997; the contents of which are incorporated herein by reference.

The x-ray projection of the markers is used to estimate the instrument-image coordinate mapping, which is then used for targeting. These algorithms compute the exact position of the target with respect to the instrument and the geometrical parameters of the imager, such as the source position, magnification factor, etc. In these procedures, distortion correction and image calibration techniques are usually required for increased accuracy. These approaches are considered to be "fully calibrated" systems and methods. See Bzosteket al., supra; Jao J., Taylor, R. H., Goldberg, R. P., Kumar, R, Bzostek, A., Van Vorhis, R., Kazanzides, P., Guezniec, A., Funda, J., "A progressive Cut Refinement Scheme for Revision Total Hip Replacement Surgery Using C-arm Fluoroscopy", lecture Notes in Computer Science, MICCAI 1999, pp. 1010–1019; the contents of which are incorporated herein by reference.

Thus, there is a need for new and improved image based target guiding systems and methods that take advantage of commonly available imaging technology and solve problems with the prior art.

SUMMARY OF THE INVENTION

According to an embodiment of the present invention, an "uncalibrated" system and method are provided for accurate needle placement without precise camera/imager calibration.

According to an embodiment of the present invention, system for image guided instrument targeting is provided. The system includes a robot unit coupled with an instrument, an imaging unit, and a first control unit, which is coupled with the robot unit and coupled with the imaging unit. The control unit receives the imaging data about a target and about the instrument from the imaging unit and controls the robot unit to properly orienting the instrument for insertion, based upon the imaging data.

According to an embodiment of the present invention, a method is provided for guiding an instrument to a target position. The method includes a steps of orienting an imager in a first imager orientation to image a target and an instrument to create first imaging data about the target and the instrument. Next, alignment of the instrument is performed in a first view, based on the first imaging data. Then, the imager is oriented in a second imager orientation to image the target and the instrument to create second imaging data about the target and the instrument. Alignment of the instrument is performed in a second view, based on the second imaging data. The first orientation and the second orientation are dissimilar orientations.

According to another embodiment of the present invention, a system is provided for image guided instrument targeting. The system includes a robot means for holding and positioning an instrument, an imaging means for imaging an area and providing imaging data and a first control means coupled with the robot means and the imaging means, for receiving imaging data about a target and about the instrument from the imaging means and for controlling said robot means to properly orient the instrument based upon the imaging data The present invention provides robot targeting system and methods under portable x-ray fluoroscopy based on image servoing. The systems and methods may be implemented for needle alignment in percutaneous procedures and may use state of the art, modular surgical robots. Such robots may include a passive arm, a low DOF (degrees of freedom) active arm surgical robot, and a needle driver.

According to an embodiment of the present invention, systems and methods are provided to directly perform targeting by using a marker located on the robot/end-effector and perform fluoroservoing under continuous imaging. Three-dimensional targeting may be achieved by performing the alignment in two dissimilar views, which are acquired at arbitrary C-Arm orientations.

According to an embodiment of the present invention, automated alignment of the needle towards a specified target can be achieved. Needle insertion can then controlled by using side-view fluoroscopic feedback. The invention offers increased accuracy, simplicity, and repeatability.

BRIEF DESCRIPTION OF THE DRAWINGS

The objects and features of the invention will be more readily understood with reference to the following description and the attached drawings, wherein:

FIGS. 2–2b are schematic representations; and

DETAILED DESCRIPTION OF THE PREFERRED EMBODIMENTS

Figure 1:
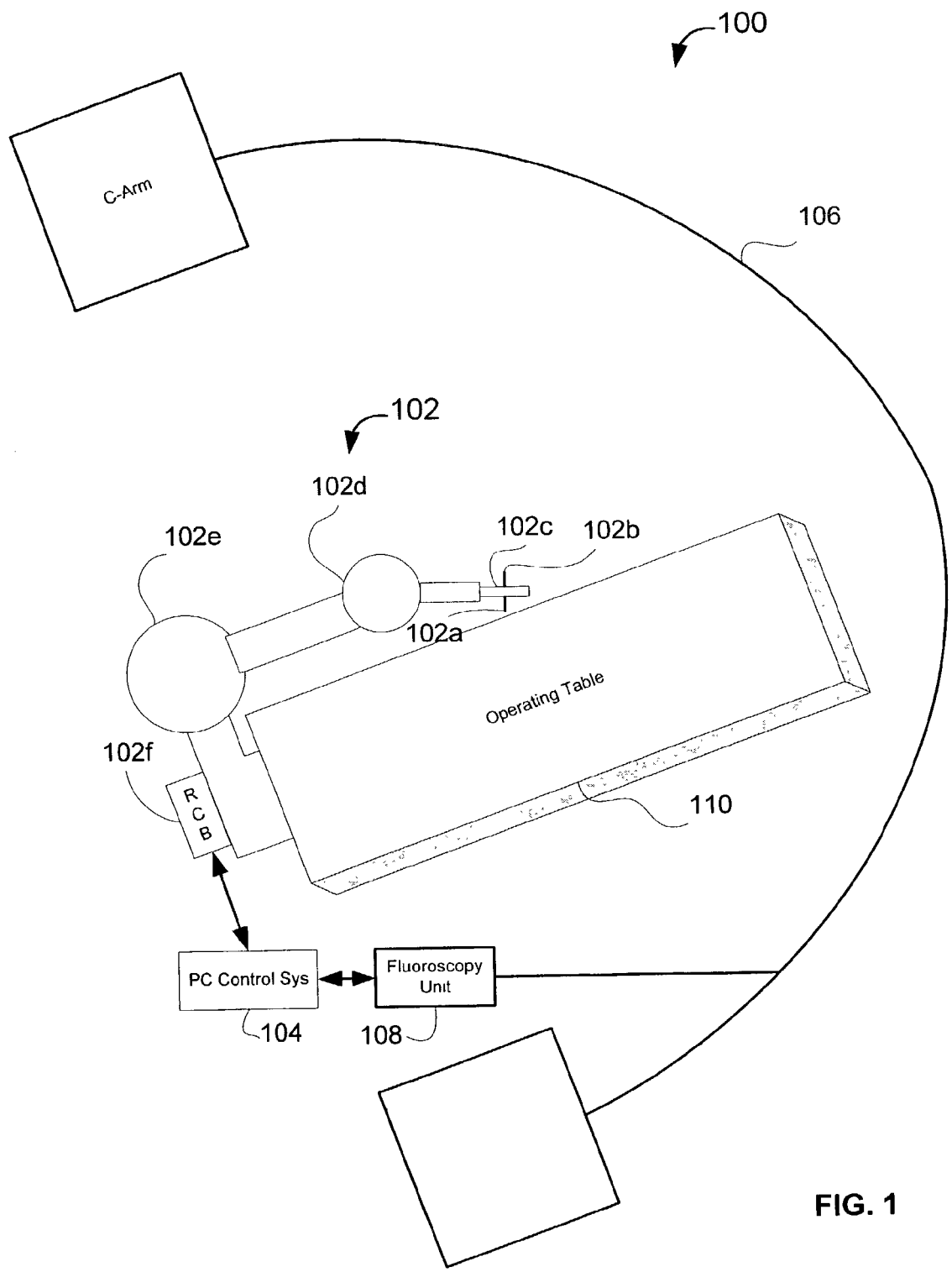
FIG. 1 is a block diagram of an image-servoing instrument guidance system according to an embodiment of the present invention.

For a discussion of the advantages and disadvantages of "uncalibrated" vision methods, see Hager, G., Hespanha, J., Dodds, Z., Morse, A. S., "What Tasks Can Be Performed with an Uncalibrated Stereo Vision System?", IJCV 35(1): pp. 65–85, November 1999, the contents of which are incorporated herein by reference.

The "uncalibrated" approach is based upon a technique in use by experienced surgeons in performing manual needle access under fluoroscopy. Based on this technique, a targeting method for percutaneous needle access based on the needle superimposition over the target, calyx of the kidney, was developed. See Stoianovivi et al. (1997), supra.

This method was implemented using a Percutaneous Access of the Kidney (PAKY) needle driver and then updated with the addition of the Remote Center of Motion (RCM) robot and a GREY supporting arm. See Stoianovici, D., Witcomb, L. L., Anderson, J. H., Taylor, R. H., Kavoussi, L. R.: "A Modular Surgical Robotic System for Image Guides Percutaneous Procedures", 1998 MICCAI, Lecture Notes in Computer Science, Springer-Verlag, Vol. 1496, pp. 404–410, 1998; Lerner, G., Stoianovici, D., Whitcomb, L., L., Kavoussi, L., R., (1999), "A Passive Positioning and Supporting Device for Surgical Robots and Instrumentation", medical Image Computing and Computer-assisted Intervention, September 1999, Cambridge, England: Lecture Notes in Computer Science, Springer-Verlag, Vol. 1679, pp. 1052–1061; the contents of which are incorporated herein by reference.

The method has proved to offer a substantial improvement over the manual approach. However, targeting is still performed by the surgeon controlling the robot. See Cadeddu, J. A., Stoianovici, D., Chen, R. N., Moore, R. G., Kavoussi, L. R., (1998), "Stereotactic mechanical percutaneous renal access", Journal of Endorology, Vol. 12, No. 2, April 1998, p. 121–126; the contents of which are incorporated herein by reference.

According to an embodiment of the present invention, a computer-controlled image-guidance system and process are provided for automated targeting using a similar system. The system and method of the present invention uses fuoroservoing (robot control based on direct image feedback from the C-Arm) in two arbitrary image views acquired at dissimilar C-Arm orientations. Certain guidance techniques have been successfully used for industrial robot guidance based on video camera images. See Batista, J., Araujo, H., Almeida A. T.: "Iterative multistep explicit camera calibration", IEEE Transactions on Robotics and Automation, Vol. 15, No. 5, October 1999, p. 897; Bernadero, A., Victor, J. S., "Binocular Tracking: Integrating perception and control", IEEE Transactions on Robotics and Automation, Vol. 15, No. 6, December 1999; Hsu, L., P. L. S.: "Adaptive visual tracking with uncertain manipulator dynamics and uncalibrated camera", Proceedings of the 38th IEEE Conference on Decision and Control (1999), p. 5, Vol. (xvii+5325); Hager, G., Hutchinson, G., and Corke, P. A Tutorial Introduction to Visual Servo Control IEEE Transactions on Robotics and Automation, 12(5), pp. 651–670, 1996; Molis, E., Chaumette, F., Boudet, S.: "2½-D Visual Servoing", IEEE Transactions on Robotics and Automation. Vol.15, No. 2, April 1999, p. 238; the contents of which are incorporated herein by reference.

According to an embodiment of the present invention, a system 100 for image-based targeting is shown in FIG. 1. System 100 may include a surgical robot 102 for physically moving an instrument, such as a needle, a PC 104 for performing image processing and robot control, a C-Arm imager 106 connected with a fluoroscopy unit 108, and an operating room table 110. The C-Arm imager 106 may be, for example, a digital C-Arm (OEC-9600) and provides x-ray images. The C-arm imager 106 and fluoroscopy unit 108 communicate with and may be controlled by PC 104. Accordingly, the PC 104 can be configured to acquire the image, such as via a video card (e.g., Matrol Meteor™). The robot 102 may be attached to the table 110 by a slide rail or other, preferably adjustable mount, and controlled by PC 104 using a real-time motion control card (e.g., PCX-DSP8, by Motion Engineering, Inc.). PC 104 may include a fluoro-servoing algorithm or program that controls needle orientation based on radiological feedback from the C-arm imager 106 and fluoroscopy unit 108. One skilled in the art will readily understand that the method of the present invention may be implemented in a variety of ways including hardware, software, firmware, or a combination thereof.

Robot 102 may be a modular, surgical robot and may be configured for unrestricted motion including arm movement and rotation. An exemplary robot 102 preferably includes a passive arm 102e coupled with a three-joint low dof (degrees of freedom) active arm surgical robot 02d, coupled with a needle driver 102c. The passive arm 102e is preferably a sturdy, passive mechanical arm with high stiffness and payload, and is for moving an end effector and holding it in place for surgery. For example, a GREY arm may be used, which is shown and described in Stoanovici (1999), supra. As the end effector, a PAKY-RCM robot assembly comprising the needle driver PAKY 102c and the RCM surgical robot 102d are preferrably implemented. PAKY is a radiolucent needle driver used to guide and actively drive a trocar needle in percutaneous access procedures. Its radiolucent design allows for unobstructed visualization of the procedure needle and of an anatomical target.

PAKY drivers are constructed for a "Superimposed Needle Registration Method." According to the present invention, PAKY 102c is configured to accommodate the computer-guided fluoro-servoing algorithm, which is described in detail below. Accordingly, a thinner outline to PAKY 102c, in the shape of a rectangular bar is provided, as illustrated in FIG. 1. The RCM 102d section is a compact robot for surgical applications that implements a fulcrum point located distal to the mechanism. The RCM 102d provides unrestricted rotations about an RCM point (fulcrum point), uniform rigidity of the mechanism and eliminates singular points.

For further details regarding exemplary PAKY and RCM robots, see Stoianovivi, et al. (1997), supra; Stoianovici et al. (1998) supra.

The robot 102 can be configured to precisely orient an end-effector (i.e., surgical instrument) in space while maintaining the location of one of its points. This kinematic architecture is especially useful for applications requiring a singular entry point, such as for laparoscopy and percutaneous access.

The robot assembly (102a–102d) is supported into the passive arm 102e, which is mounted to the operating-table 110. This allows for positioning and steady support of the robot while working in close proximity of an organ to be operated on. The PAKY 102c and RCM 102d (together, the PAKY-RCM assembly) is capable of orienting a needle while maintaining its tip location (i.e., by rotation, etc.). This gives the robot 102 the ability of aiming the needle at any desired target while setting the skin insertion point and positioning the needle tip at the selected location. Thus, only two motions are thus required for orientating the needle about the fulcrum point. See Lerner et al., supra. According to the present invention, the targeting process takes advantage of this kinematic simplicity, as described below.

Fluoro-servoing is a particularization of visual servoing using x-ray fluoroscopy feedback. Visual servoing is a generic name for the class of robot control algorithms using image feedback for performing positioning and tracking operations. For example, see Batista et al., supra; Bernadero et al., supra; Hsu et al, supra; Hager et al., supra.

The main difficulty in performing portable fluoroscopy computer-assisted procedures is the lack of information regarding the pose of the imager with respect to the patient. As a mobile unit, the C-Arm 106 may be moved and reoriented during the procedure to satisfy surgical needs. According to the present invention, an accurate process for instrument (needle) targeting is provided, which is independent of C-Arm 106 orientation. The process uses image-servoing, and preferably, fluoro-servoing, to orient the needle about a fulcrum point located at its tip.

The needle 102b is aimed at a desired target utilizing a needle alignment in two dissimilar views obtained from different C-Arm 106 orientations. That is, the needle 102b is oriented so that it extends into the target in both views. Since alignments are performed sequentially, it is desired that the second alignment does not deteriorate the first alignment.

Each alignment may be performed automatically by the guidance algorithm, which corrects the needle position based on image feedback. For facilitating the automatic detection of the needle 102b into the image, the needle 102b may be equipped with a radio-opaque spherical ball (not shown) at the free end, thus providing a well-discriminated signature for the fluoroscopy unit 108. A pattern-matching algorithm running on the video acquisition board of the PC 104 may be used to rapidly locate the spherical ball marker in the x-ray image. All calculations can be performed in a fixed reference frame centered at the needle tip and oriented according to the initial position of the robot.

Figure 2:
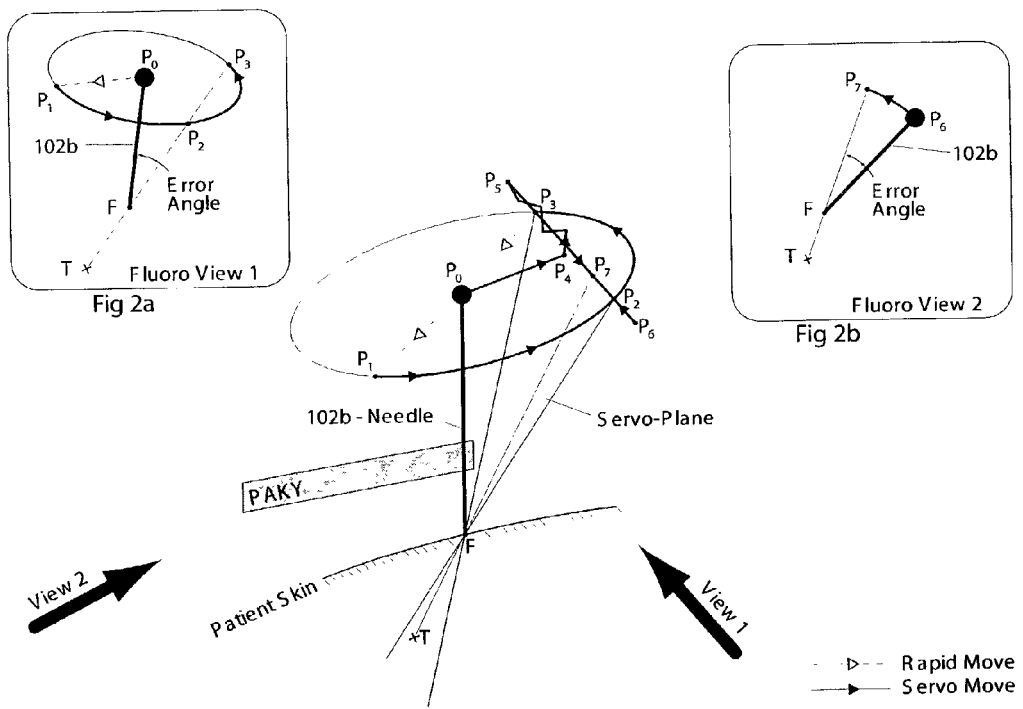
Figure 3:
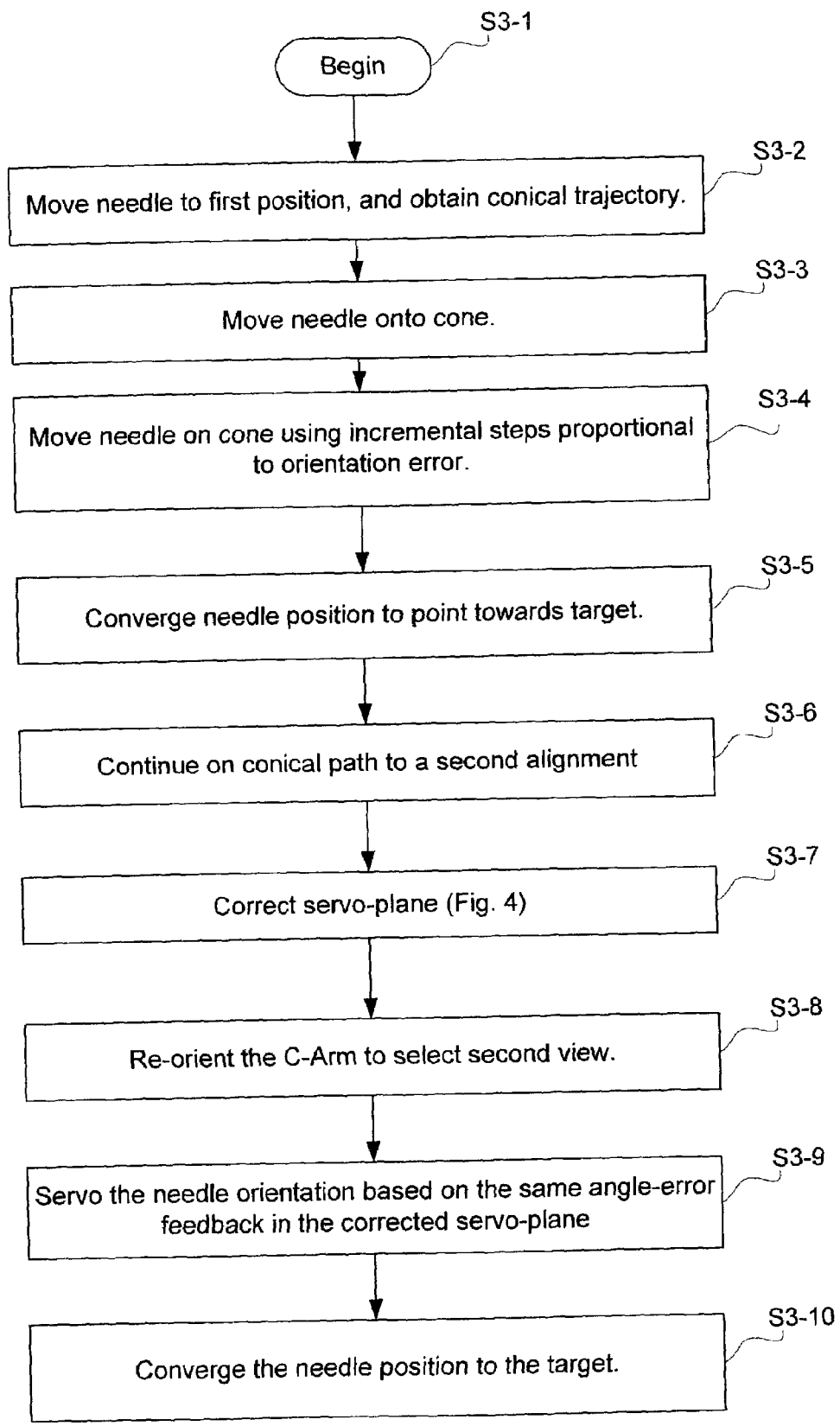
FIGS. 3 and 4 are flow charts of an exemplary process for guiding an instrument according to an embodiment of the present invention.
Figure 4:
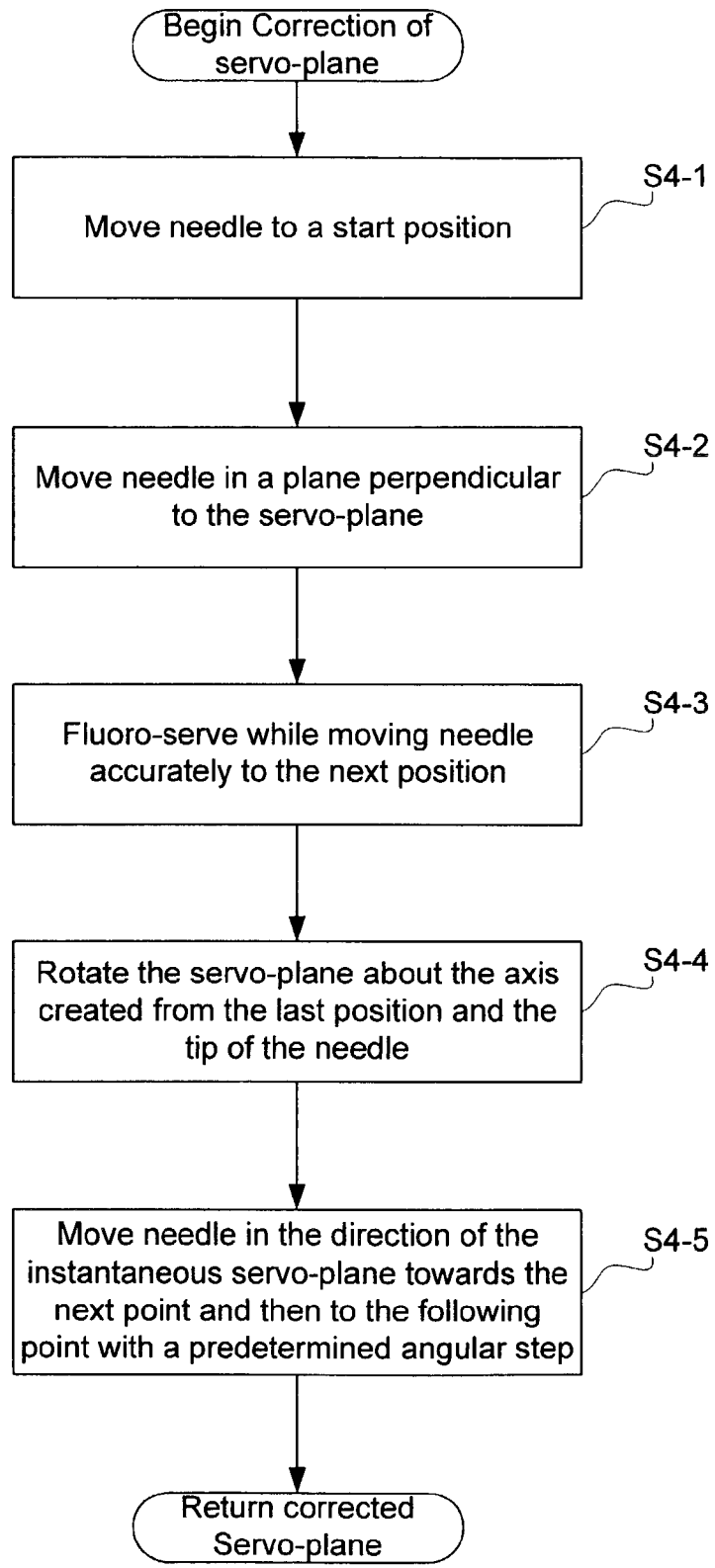

According to a preferred embodiment, operations and processing of the present invention are schematically represented in FIGS. 2–2b, and are explained with further reference to FIGS. 3 and 4.

Processing begins at step S3-1. At step S3-2, the needle 102b is supported by the PAKY driver 102c and positioned with the tip at the skin entry point (F). The central illustration is a 3-D representation whereas the two side views are x-ray projections of this space from View 1 and View 2 respectively, as indicated by the arrows. The figure presents the needle at different positions, which will be scanned during the two-phase alignment. In this motion the tip of the needle remains at the fulcrum point (F), while the needle end (the ball end) changes location from $P_0 \rightarrow P7$ as later described. The needle is initially located at $P_0$. Targeting may be achieved in principle two steps according to the C-Arm orientations View 1 and View 2, shown in FIGS. 2a and 2b, respectively.

Referring to FIG. 2a, a conical needle trajectory is used to obtain an initial estimate of the relative robot-image orientation. At step S3-3, a rapid approach move of an arbitrary direction $P_0P_1$ places the needle 102b on the cone. The cone angle is set so that the target is located within the space swept by the needle extension.

At step S3-4, starting from $P_1$, the needle is moved on the cone using incremental steps proportional to the orientation error, which is given by the angle $180°-\angle TFP_i$ measured in the x-ray projection. This proportional algorithm converges to the needle position $P_2$, in which the needle 102b at $P_2F$ points towards the target T, at step S3-5. Continuing on the conical path a second alignment is achieved at point $P_3$ in a similar manner, at step S3-6.

The plane $FP_2P_3$ is now the initial servo-plane. This plane has the property that at any position within the plane the needle 102b will maintain View 1 target alignment. When the identification accuracy of this plane is not consistent, errors may occur depending on the distance of this plane from the start point $P_0$. Explicitly, greater errors may be encountered when points $P_2$ and $P_3$ are closely located at a side of the cone.

To overcome this problem, while maintaining a minimal cone angle, the servo-plane can be corrected at step S3-7, following the $P_3 \rightarrow P_0 \rightarrow P_4 \rightarrow P_5 \rightarrow P_6$ path, as follows.

Referring to FIG. 4, at step S4-1, the needle 102b is rapidly brought to the start position $P_0$ and then moved in a plane $FP_0P_4$ perpendicular to the servo-plane, at step S4-2. Then, on this path, at step S4-3, fluoro-servoing is employed to achieve accurate needle alignment at point $P_4$. The process may use the same angle-feedback proportional control as described above with reference to steps S3-4–S3-6.

At step S4-4, the axis $FP_4$ is then used as a pivot about which the servo-plane is rotated for iterative corrections. From point $P_4$, the needle 102b is moved in the direction of the instantaneous servo-plane towards the point $P_5$ and then $P_6$ with a prescribed angular step, at step S4-5. Target alignment may be reevaluated during each step by searching transversally, and the orientation of the servo-plane can be corrected accordingly. Thus, correction is achieved by adjusting the servo-plane angle through the pivot axis $FP_4$ with an amount proportional to the angular targeting error.

The new servo plane $FP_5P_6$ is similar to the initial cone determined plane $FP_2P_3$. However, the new plane ensures that the end points $P_5$ and $P_6$ are sufficiently spaced apart to render a consistent determination of the servo-plane and also averages errors over the multiple scan points on the $P_4 \rightarrow P_5 \rightarrow P_6$ trajectory. In a preferred embodiment of the present invention, the limit points $P_5$ and $P_6$ are placed at a needle angle equal to the initial cone angle measured in the servo plane. The servo-plane ensures that independent of the needle orientation, within this plane, the needle 102b is properly aligned to the target in the first view.

Three-dimensional targeting requires the additional determination of an axis within this plane passing the fulcrum F and the target T. Referring to FIG. 2b, a second view is selected by reorienting the C-Arm 106, at step S3-8. The orientation of this plane is arbitrary except that in this view, the servo plane does not project into a line. According to a preferred embodiment, high precision is achieved by setting the view normal to the servo-plane.

At step S3-9, needle alignment is performed by servoing the needle orientation within the previously determined servo-plane based on the same angle-error feedback, as represented in the x-ray projection in FIG. 2b. At step S3-10, the algorithm converges to the needle position $FP_7$. In this orientation the target is located on the needle axis, and insertion of the needle may be accurately made.

By using the servo-plane, the second view alignment preserves the first. Three-dimensional targeting is thus obtained by combining both-2 dimensional alignments.

The robotic system 102 is preferably adapted for the above-described method. A special design of the needle driver 102c may be implemented and integrated. Such a system using the servo-targeting algorithm of the present invention was tested for accuracy and reliability using specially derived experiments and then clinically validated for percutaneous renal access.

For minimizing the radiation exposure during software design and evaluation, the process may be tested using a video camera mounted on a positioning stand (not shown). A white background and a black needle may be used for achieving proper contrast. A 2 mm spherical ball may be used represent the target. Repeated tests revealed a targeting accuracy not greater than 0.5 mm.

Imager distortion may be evaluated by constructing a template of equally spaced steel balls mounted on a thin radiolucent-plate. For an OEC-9000 imager, the overall distortion should be under 0.75 mm in a region next to the image center, including the error of the ball-finder algorithm. The magnification function of the fluoroscope allows for maintaining the field of view in the reduced distortion zone around the image center. Using a 2 mm ball target located 80 mm below the needle tip (fulcrum/skin entry point) the image guidance process of the present invention should have an error under 1.5 mm. The safety of the system for surgical applications is inherited from the kinematic design of the robotic component.

The PAKY-RCM assembly of the present invention provides decoupled orientation and needle insertion capabilities allowing for independent activation of the two stages. This insures that the needle may not be inadvertently inserted during the orientation stage and accidental reorientation may not occur during needle insertion. See Stoianovici et al. (1998), supra.

See also, Bauer J. J., Stoianovici D., Lee B. R., Bishoff J., Caddeu J. A., Whitcomb L. L., Taylor R. H., Macali S., Kavoussi L. R., (1999), "Transcontinental Telesurgical Robotic Percutaneous Renal Access: Case Study", American Telemedicine Association (ATA) conference, Salt Lake City, Utah, Abstract #18D, Apr. 18–21, 1999, Telemedicine Journal, 5(1):27:1999, the contents of which are hereby incorporated by reference.

The fluoro-servoing targeting system and method of the present invention may be implemented for percutaneous renal access as well. For renal access, the operating room and the patient may be prepared as for the standard procedure. The patient is preferably placed under total anesthesia. The fluoroscopy table 110 may be equipped with a special rigid rail. The robot 102 may be mounted onto the rail on the side of the targeted kidney and covered with a sterile bag. The needle driver 102c is sterilized prior to the operation. As for the manual procedure, the C-Arm 106 may be positioned on the opposite side of the table and all steps prior to the needle access are performed as already described above with reference to FIGS. 2, 2a and 2b.

First, the skin insertion point may be chosen as normally done in a manual procedure, and the robot assembly 102 may be positioned by manipulating the passive arm such that the needle tip (located at the fulcrum point of the RCM) is located at the chosen point. The C-Arm 106 should be oriented for proper kidney and needle visibility. Then, the target calyx is identified on the PC monitor by manually selecting a point on the image. The first view needle alignment is then automatically performed by the system 100. The C-Arm 106 is then rotated to a dissimilar view in which the target can be identified again. The second needle alignment is automatically performed by system 100. Using other C-Arm orientations, the needle targeting and can be verified needle insertion can be performed under direct lateral observation.

In all steps, patient respiration is preferably shortly stopped during the image acquisition prior to target selection and during needle insertion. The patient may breathe in all other stages including servo targeting.

In a clinical test, the kidney was accessed on the first targeting attempt in less than 10 minutes. The needle, however, needed to be slightly retracted and reinserted again, as it initially pushed the kidney aside due to tissue deflection and needle bowing. This was not caused by targeting errors, since the small retraction and reinsertion properly aimed the target. This problem was also encountered due to the fact that for this patient, the target was located on a peripheral lower pole calyx.

The total radiation exposure time of the patient during this procedure was 90 seconds. Exposures could be reduced by commanding the imager to strobe activate during the servo motion. Even without strobing, the total radiation can be significantly reduced as compared to the common manual approach, due to the fact that the system and method of the present invention offer well-defined step-by-step algorithm eliminating the need for the problematic surgeon interpretation of volumetric anatomy.

An exemplary ball-finder algorithm may be implemented in hardware, such as by a Martox card™.

Although the invention has been described based upon these preferred embodiments, it would be apparent to those of skilled in the art that certain modifications, variations, and alternative constructions would be apparent, while remaining within the spirit and scope of the invention. In order to determine the metes and bounds of the invention, therefore, reference should be made to the appended claims.

For example, the system and method of the present invention may be implemented in urology as well as other medical fields. The system and method may also prove useful for applications involving similar imaging equipment such as biplanar fluoroscopy units.

We claim:

1. A method for guiding an instrument to a target position, said method comprising steps of:
   orienting an imager in a first imager orientation to image a target and an instrument to create first imager-orientation imaging data about said target and said instrument;
   placing said instrument in an initial position with a fulcrum end of the instrument at a fulcrum point;
   moving a moveable end of the instrument alone a curve while maintaining the fulcrum end of the instrument at the fulcrum point, whereby the instrument moves along a conical trajectory;
   determining a servo-plane based on the first imager-orientation imaging data taken while moving the instrument along the conical trajectory;
   orienting said imager in a second imager orientation to image said target and said instrument to create second imager-orientation imaging data about said target and said instrument; and
   performing allignment of said instrument in a second view while maintaining the instrument in the servo-plane, based on said second imager-orientation imaging data;
   wherein said first orientation and said second orientation are dissimilar.

2. The method according to claim 1, wherein:
   said alignment of said instrument in said first view and said second view are performed under constant imaging.

3. The method according to claim 1, wherein:
   said alignment of said instrument in said first view and said second view are performed under strobed imaging.

4. The method according to claim 1, wherein:
   said imager is a portable C-arm fluoroscope.

5. The method according to claim 4, wherein:
   said alignment of said instrument in said first view and said second view is performed under a fluoro-servoing, utilizing feedback of said first and second imaging data.

6. The method according to claim 5, further comprising the step of:
   calculating an orientation error during said fluoro-servoing, said orientation error being based on an angle formed by an axis and a edge of the conical trajectory of said instrument;
   and wherein said alignment of said instrument in said first view and said second view is further based on said orientation error.

7. The method according to claim 6, further comprising the step of:
   correcting a servo-plane of said instrument before orienting said imager in said second imager orientation.

8. The method according to claim 6, wherein said first alignment step and said second alignment step include incrementally moving said instrument on said conical trajectory using incremental steps proportional to the orientation error.

9. The method according to claim 1, further comprising:
   calculating said desired alignment of said needle by performing alignment in two dissimilar views, which are acquired from said imaging unit in two arbitrary C-Arm orientations.

10. The method according to claim 1, further comprising:
    marking an end-effector during imaging, wherein said imaging data includes location data of said end-effector, and the orientation of said instrument is based on said location data.

* * * * *